(12) United States Patent
Ben-Ari et al.

(10) Patent No.: US 10,650,286 B2
(45) Date of Patent: May 12, 2020

(54) CLASSIFYING MEDICAL IMAGES USING DEEP CONVOLUTION NEURAL NETWORK (CNN) ARCHITECTURE

(71) Applicant: International Business Machines Corporation, Armonk, NY (US)

(72) Inventors: Rami Ben-Ari, Kiryat Ono (IL); Pavel Kisilev, Maalot (IL); Jeremias Sulam, Baltimore, MD (US)

(73) Assignee: International Business Machines Corporation, Armonk, NY (US)

( * ) Notice: Subject to any disclaimer, the term of this patent is extended or adjusted under 35 U.S.C. 154(b) by 189 days.

(21) Appl. No.: 15/697,454

(22) Filed: Sep. 7, 2017

(65) Prior Publication Data
US 2019/0073569 A1    Mar. 7, 2019

(51) Int. Cl.
*G06K 9/00* (2006.01)
*G06K 9/62* (2006.01)
*G06N 3/04* (2006.01)
*G06N 3/08* (2006.01)
*G06K 9/46* (2006.01)
(Continued)

(52) U.S. Cl.
CPC .......... *G06K 9/6269* (2013.01); *A61B 5/0091* (2013.01); *A61B 5/055* (2013.01); *A61B 5/7264* (2013.01); *A61B 5/7267* (2013.01); *A61B 5/7282* (2013.01); *A61B 6/502* (2013.01); *A61B 6/5217* (2013.01); *G06K 9/4642* (2013.01); *G06K 9/6271* (2013.01); *G06N 3/04* (2013.01); *G06N 3/08* (2013.01); *G16H 30/40* (2018.01); *G16H 50/20* (2018.01); *G16H 50/70* (2018.01); *G06K 9/6284* (2013.01); *G06K 2209/05* (2013.01)

(58) Field of Classification Search
None
See application file for complete search history.

(56) References Cited

U.S. PATENT DOCUMENTS

2015/0110387 A1    4/2015  Lienhart et al.
2017/0161545 A1*   6/2017  Champlin ............ G06K 9/0014
(Continued)

OTHER PUBLICATIONS

Hwang et al., "Self-Transfer Learning for Fully Weakly Supervised Object Localization", arXiv:1602.01625 [cs.CV], 2016.
(Continued)

*Primary Examiner* — Wei Wen Yang
(74) *Attorney, Agent, or Firm* — Gregory J. Kirsch

(57) ABSTRACT

Embodiments of the present systems and methods may provide the capability to classify medical images, such as mammograms, in an automated manner using existing annotation information. In embodiments, only the global, image level tag may be needed to classify a mammogram into certain types, without fine annotation of the findings in the image. In an embodiment, a computer-implemented method for classifying medical images may comprise receiving a plurality of image tiles, each image tile including a portion of a whole view, processed by a trained or a pre-trained model and outputting a one-dimensional feature vector for each tile to generate a three-dimensional feature volume and classifying the larger image by a trained model based on the generated three-dimensional feature volume to form a classification of the image.

20 Claims, 5 Drawing Sheets

(51) Int. Cl.
   *A61B 5/055*   (2006.01)
   *A61B 6/00*    (2006.01)
   *A61B 5/00*    (2006.01)
   *G16H 30/40*   (2018.01)
   *G16H 50/70*   (2018.01)
   *G16H 50/20*   (2018.01)

(56) References Cited

U.S. PATENT DOCUMENTS

2017/0161891 A1* 6/2017 Madabhushi ......... G06T 7/0012
2018/0018757 A1* 1/2018 Suzuki ................. G06T 3/4046

OTHER PUBLICATIONS

Cao et al., "Ensemble-based hybrid probabilistic sampling for imbalanced data learning in lung nodule CAD", Computerized Medical Imaging and Graphics, Apr. 2014, pp. 137-150, vol. 38, Issue 3.
Arevalo et al., "Representation learning for mammography mass lesion classification with convolutional neural networks", Computer Methods and Programs in Biomedicine, Apr. 2016, pp. 248-257, vol. 127.
Jiao et al., "A deep feature based framework for breast masses classification", Neurocomputing, Jul. 12, 2016, pp. 221-231, vol. 197.
Kooi et al., "Large scale deep learning for computer aided detection of mammographic lesions", Medical Image Analysis, Jan. 2017, pp. 303-312, vol. 35.
Levy et al., "Breast Mass Classification from Mammograms using Deep Convolutional Neural Networks", arXiv:1612.00542v1 [cs.CV], 2016.
Shin et al., "Deep Convolutional Neural Networks for Computer-Aided Detection: CNN Architectures, Dataset Characteristics and Transfer Learning", IEEE Transactions on Medical Imaging May 2016, vol. 35, No. 5, May 2016.
Ataman et al., "Optimizing Area Under the ROC Curve using Ranking SVMs", In Proceedings of International Conference on Knowledge Discovery in Data Mining, 2005.
Cortes et al., "AUC Optimization vs. Error Rate Minimization", Proceedings of the 16th International Conference on Neural Information Processing Systems, Dec. 2003, pp. 313-320.
Ding et al., "Adaptive Subgradient Methods for Online AUC Maximization", arXiv:1602.00351v1 [cs.LG], 2016.
Gao et al., "One-Pass AUC Optimization", International Conference on Machine Learning, Jun. 2013, pp. 906-914 vol. 28.
Herschtal et al., "Optimising Area Under the ROC Curve Using Gradient Descent", Proceedings of the 21st International Conference on Machine Learning, Banff, Canada, 2004.
Huang et al., "Learning Deep Representation for Imbalanced Classification", 2016 IEEE Conference on Computer Vision and Pattern Recognition, Jun. 2016, pp. 5375-5384.
Wang et al., "AUC-Maximized Deep Convolutional Neural Fields for Protein Sequence Labeling", ECML PKDD 2016: Machine Learning and Knowledge Discovery in Databases, 2016, pp. 1-16.
Zhao et al., "Online AUC Maximization", Proceedings of the 28th International Conferenceon Machine Learning, 2011, pp. 233-240.
Eban et al., "Scalable Learning of Non-Decomposable Objectives", Proceedings of the 20th International Conference on Artificial Intelligence and Statistics (AISTATS) 2017.
Castro et al., "Improving ANNs Performance on Unbalanced Data with an AUC-Based Learning Algorithm", Proceedings of the 22nd international conference on Artificial Neural Networks and Machine Learning, Sep. 2012, pp. 314-321, vol. 2.
Zhu et al., "Deep Multi-instance Networks with Sparse Label Assignment for Whole Mammogram Classification", Medical Image Computing and Computer-Assisted Intervention, Sep. 2017, pp. 603-611.

* cited by examiner

CLASSIFYING MEDICAL IMAGES USING DEEP CONVOLUTION NEURAL NETWORK (CNN) ARCHITECTURE

BACKGROUND

The present invention relates to techniques and a framework for classifying medical images, such as mammograms, with weakly labeled (such as without local annotations of the findings) and imbalanced data sets, using deep convolution neural network (CNN) architecture.

Automated recognition of abnormalities in medical images has become an important medical diagnostic tool. Typically, automated recognition techniques are directed toward recognizing medical images containing a certain type of abnormality, and separating (classifying) them from the rest. Several conventional solutions have been proposed, which attempt to facilitate the diagnostic procedure by radiologists. Many of these approaches consist of a two-stage process: an initial detection or localization of potential abnormal candidates, and the posterior classification of the candidate belonging to a certain class. In mammography, these machine learning based methods rely on finely annotated data, requiring manual labeling that shows the lesion location in the image and often delineation of the boundaries. Such annotation is rarely available as current and past radiologist work flow does not digitally record this data in the system. The alternative of re-examining the entire data set for annotation can be extremely expensive, often making this process infeasible. However, the severity score or final diagnosis based on each mammogram is typically accessible via the medical records, and can be used as a global label for the whole mammogram.

Accordingly, a need arises for techniques by which medical images, such as mammograms, may be classified (for example as malignant versus Normal or benign) in an automated manner with minimal requirement for data annotation.

SUMMARY

Embodiments of the present systems and methods may provide the capability to classify medical images, such as mammograms, in an automated manner using a global image-tag, namely without requiring local annotations of any finding in the image. This information, for example BIRADS (Breast Imaging Reporting and Data System) is commonly available in the medical records without additional annotation labor. In embodiments, only the global, image level tag is needed to classify a mammogram into certain types, without detailed annotation of the findings in the image, usually describing their position, shape and type.

In an embodiment, a computer-implemented method for classifying medical images with a global image-level tag and without local annotations that reveal a position and a shape of findings within the image may comprise receiving a plurality of image tiles from a whole image, each image tile including a portion of the whole image, processed by a trained or a pre-trained model and outputting a one-dimensional feature vector for each tile to generate a three-dimensional feature volume, and classifying the whole image by a trained model based on the generated three-dimensional feature volume to form a classification of the image.

In embodiments, the image may be one of a mammogram image or a breast Magnetic Resonance Imaging image. The classification may be a binary classification that classifies the images into malignant or benign. The class populations may be highly imbalanced. One can unite several low severity findings into a benign-negative set and those with high severity or biopsy proven malignancy into malignant-positive set. That is, in the exemplary binary classification detailed above, the global, image level tag of the image can be either benign or malignant according to the maximum severity of the findings in the MG image. The MG sets can equally be divided to several severity classes. Additionally, the class populations are highly imbalanced. That is, the population of one class, for instance, the benign tagged images, is much larger than the population of the other class, for instance the malignant tagged images. For example, the percentage of image globally tagged as malignant can be relatively low. The three-dimensional feature volume may be generated using a plurality of layers of convolutional network processing in a deep convolutional neural network, wherein the deep convolutional neural network may use a deep neural network loss function that directly maximizes an area under the curve (AUC) performance measure. The deep convolutional neural network may combine a tile based approach with pre-trained encoding and trained convolutional neural network layers. Sizes of the tiles may be determined based on an expected size of findings in the images.

In an embodiment, a system for classifying medical images with a global image-level tag and without local annotations that reveal a position and a shape of findings within the image may comprise a processor, memory accessible by the processor, and computer program instructions stored in the memory and executable by the processor to perform receiving a plurality of image tiles from a whole image, each image tile including a portion of the whole image, processed by a trained or a pre-trained model and outputting a one-dimensional feature vector for each tile to generate a three-dimensional feature volume and classifying the whole image by a trained model based on the generated three-dimensional feature volume to form a classification of the image.

In an embodiment, a computer program product for classifying medical images with a global image-level tag and without local annotations that reveal a position and a shape of findings within the image may comprise a non-transitory computer readable storage having program instructions embodied therewith, the program instructions executable by a computer, to cause the computer to perform a method comprising: receiving a plurality of image tiles from a whole image, each image tile including a portion of the whole image, processed by a trained or a pre-trained model and outputting a one-dimensional feature vector for each tile to generate a three-dimensional feature volume and classifying the whole image by a trained model based on the generated three-dimensional feature volume to form a classification of the image.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION

Embodiments of the present systems and methods may provide the capability to classify medical images, such as mammograms or breast MRI, in an automated manner using weak annotation information. In embodiments, only the global, image level tag may be needed to classify a mammogram into certain types, without local annotation of the findings in the image.

In embodiments, a model may be built that distinguishes between features derived from a malignant finding within an image and other features resulting from normal or benign findings. Since the location of the finding is unknown, the image may be divided into tiles (with overlap). These image tiles may then be given a rich representation by using a pre-trained network (trained on ImageNet). Given sufficient data the pre-trained network may be replaced with a trainable model. A convolutional net may be designed to apply on the representation tensor and output a class corresponding to a certain type. In embodiments, a number of classification types may be generated. For example, a binary classification of mammogram images may generate images globally tagged with labels such as malignant (positive) vs. benign/normal (negative).

In embodiments, the problem of imbalanced data may be addressed. Typically, the size of the positive set (containing a certain illness) is significantly less than the negative set. In embodiments, a novel loss function may be used for the convolutional networks. Frequently, the convolutional networks are optimized for classification accuracy while the actual performance is measured by Area Under the (ROC) Curve—AUC (which is a normalized measure). In embodiments, the novel loss function for the convolutional networks may directly maximize the AUC measure, resulting in improved AUC when compared to conventional classification accuracy measure.

Figure 1:
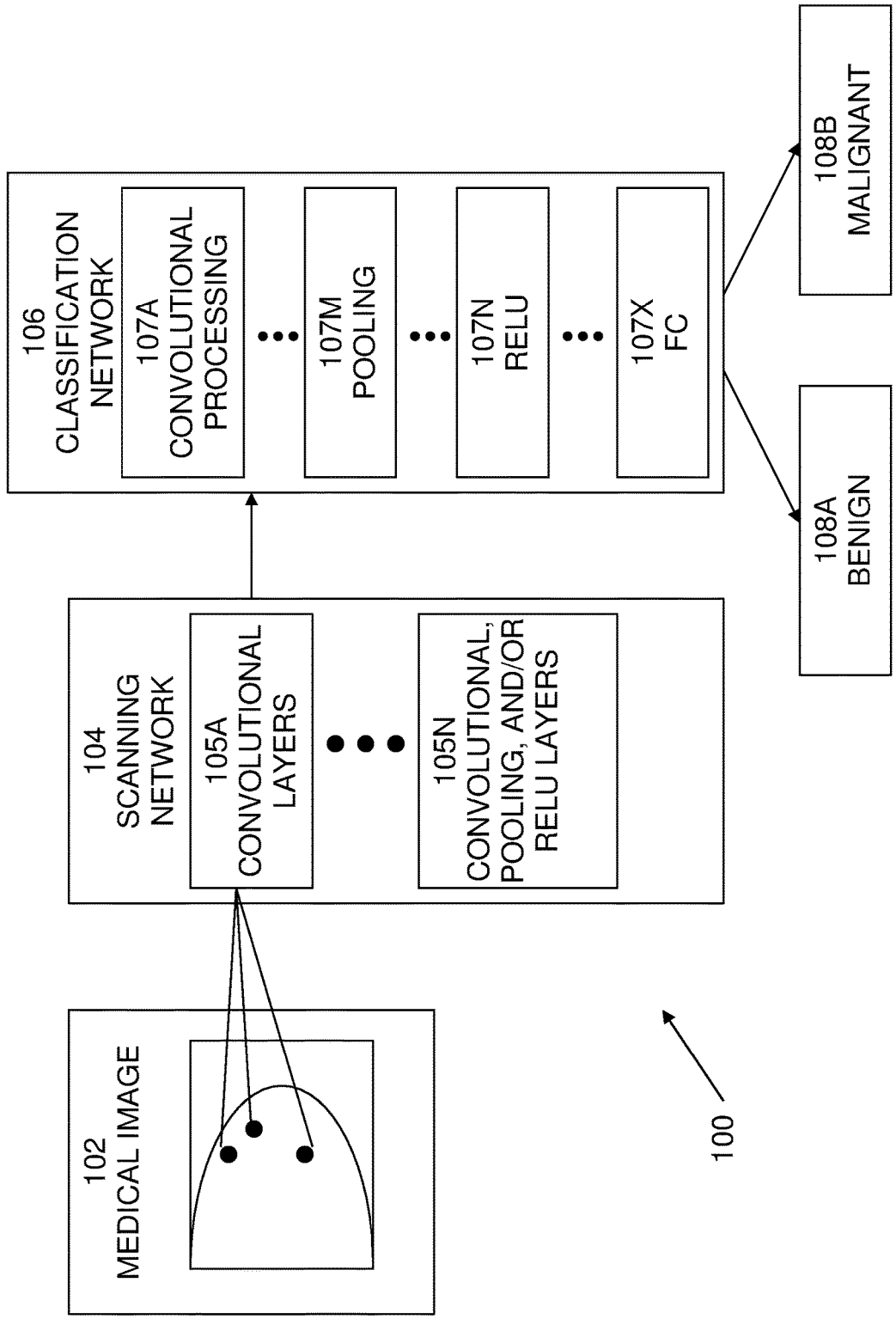
FIG. 1 illustrates an exemplary system in which described embodiments may be implemented.
Figure 2:
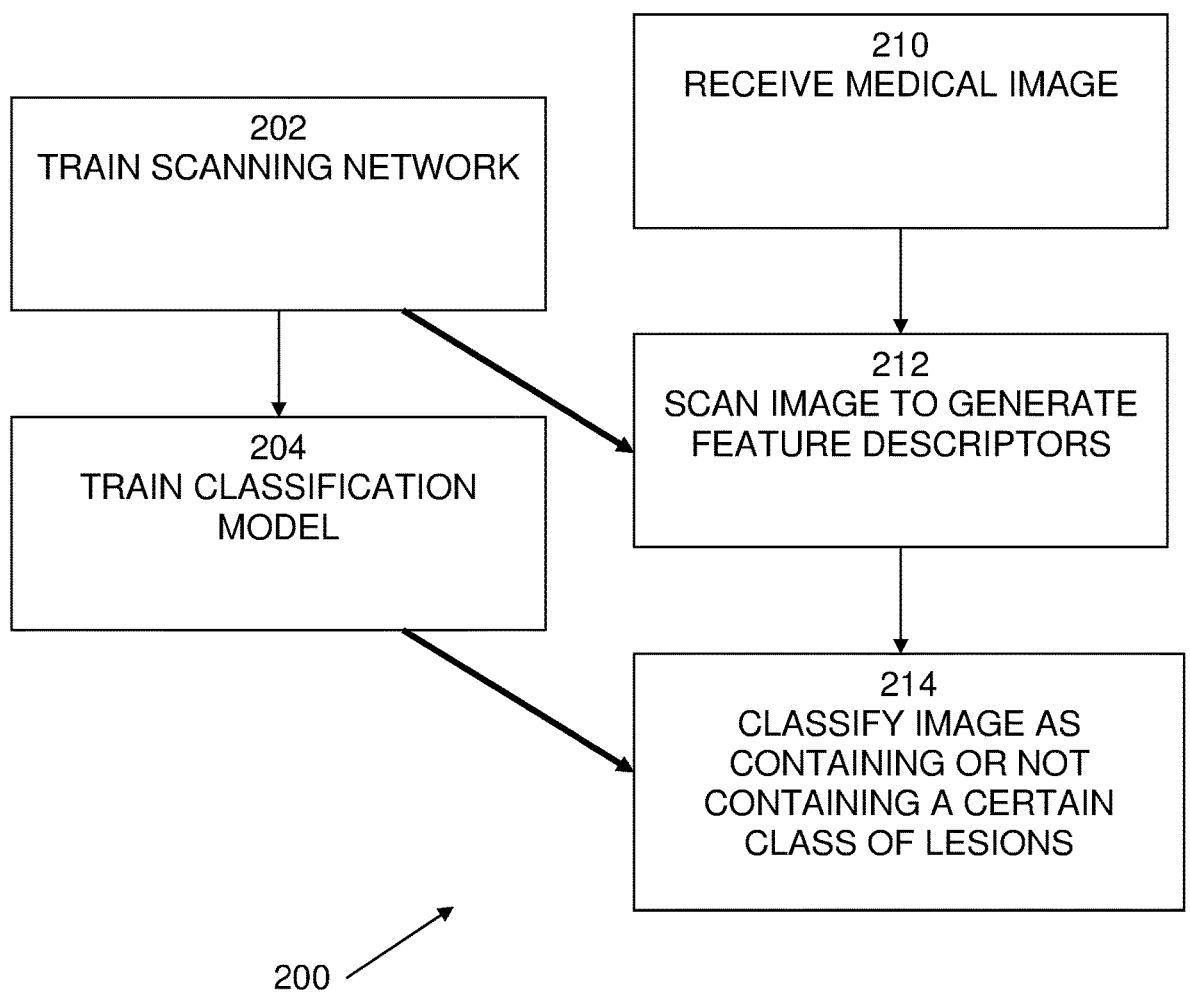
FIG. 2 illustrates an exemplary flow diagram of a process of image classification.

An exemplary system 100, in which embodiments of the described techniques may be implemented, is shown in FIG. 1. It is best viewed in conjunction with FIG. 2, which is an exemplary flow diagram of a process of image classification 200. System 100 may include a received medical image 102, a scanning network 104, and a classification network 106. While for clarity, scanning network 104 and classification network 106 are described separately, they may also be understood as both integrated within a complete deep convolutional neural network. Scanning network 104 may include a plurality of layers, such as convolutional, pooling, and or REctifying Linear Units (RELU) layers 105A-N, while classification network 106 may include processing layers such as convolutions 107A, max-pooling operations 107M, REctifying Linear Units (RELUs) 107N and fully connected networks 107X. Classification network 106 may generate a label for the whole mammogram, associating it to the class of normal or containing a benign lesion mammogram 108A or to the sever class of mammograms containing some type of malignant lesion 108B.

Process 200 may begin with 202, in which the scanning network may be trained. In embodiments, scanning network 104 may be a convolutional neural network that provides feature descriptors of local areas in the mammogram. In embodiments, scanning network 104 may be configured and trained using standard or purpose-generated convolutional neural networks and training data. For example, in embodiments, the convolutional neural networks from the Visual Geometry Group (VGG) at Oxford University, trained on natural images may be used. VGG provides a deep convolutional network for object recognition that has already been trained. In embodiments, scanning network 104 may be trained using external data or end-to-end, by standard or custom data sets. The present techniques are applicable to any arrangement of provision and training of convolutional neural networks.

In 204, the classification model may be trained. For example, classification network 106 may be trained, while possibly fine-tuning scanning network 104, provided access to a dataset of training images with positive and negative labels. The particular design of the network may provide the capability to circumvent the need for local labels. For example, local labels including information such as the location, contour, or other information about the may not be required, as only the global label may be used to train the entire architecture. In embodiments, and to speed-up training, the training of the first scanning network may be frozen and only the weights and biases of the second network may be adapted. This may be efficiently done by pre-computing the volumetric representations of all images in the training set, and then using these as training data. After a certain number of training epochs, both networks may be merged back together and the training continued, in order to improve performance while fine-tuning.

In 210, medical image 102 may be received by scanning network 104. Received medical image 102 typically may be a digital image received from a medical imaging system or a medical database system for classification. Received medical image 102 may be in any standard, non-standard, proprietary, or non-proprietary image format or file format. In embodiments, received medical image 102 may be a mammogram generated by a digital or digitized X-ray image. In embodiments, received medical image 102 may be any digital or digitized medical image generated by any medical imaging technology, such as X-ray, CT, MRI, etc. Received medical image 102 may be weakly labeled, that is only the global, image-level tag may be included with received medical image 102.

Figure 3:
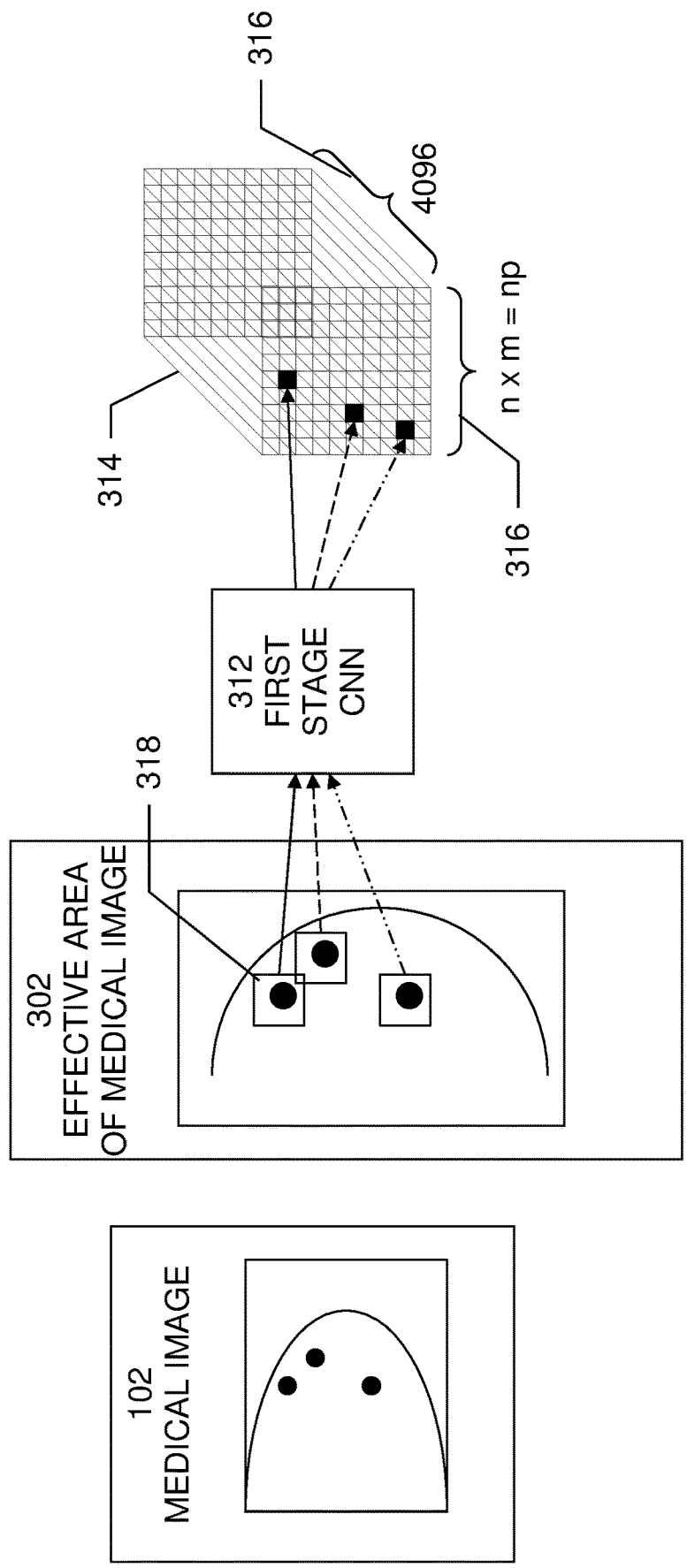
FIG. 3 illustrates an exemplary diagram of a stage of a process of image classification.

In 212, scanning network 104 may perform a scanning analysis of received medical image 102. For the example of the VGG network, embodiments may use a number of convolutional layers 105A-N, for example, the first 5 convolutional layers, of the VGG medium network to implement scanning network 104. For example, the VGG M-CNN model may be used. Because of its convolutional properties, scanning network 104 may scan the entire image 102 or the effective area of the image 302 to generate a feature vector of fixed size per image tile or local window 318. An example of this stage of processing is shown in FIG. 3. In this example, entire image 102 or the effective area of the image 302 may be scanned by first stage CNN 312 to generate a feature vector 314. In this example, each tile 318 may generate a one-dimensional feature vector 314 that is, for example, 4096 features long 316. A number, n×m=np, of tiles may be considered in each vertical and horizontal direction. For example, n×m=15×15 may be used. It is to be noted that the dimensions n and m do not need to be the same value. These features, which represent and characterize a local neighborhood, may then be grouped together to form a three-dimensional feature volume, which is a volumetric representation of the entire image. This particular aggregation strategy may ensure the spatial proximity of feature originated from proximal regions.

Figure 4:
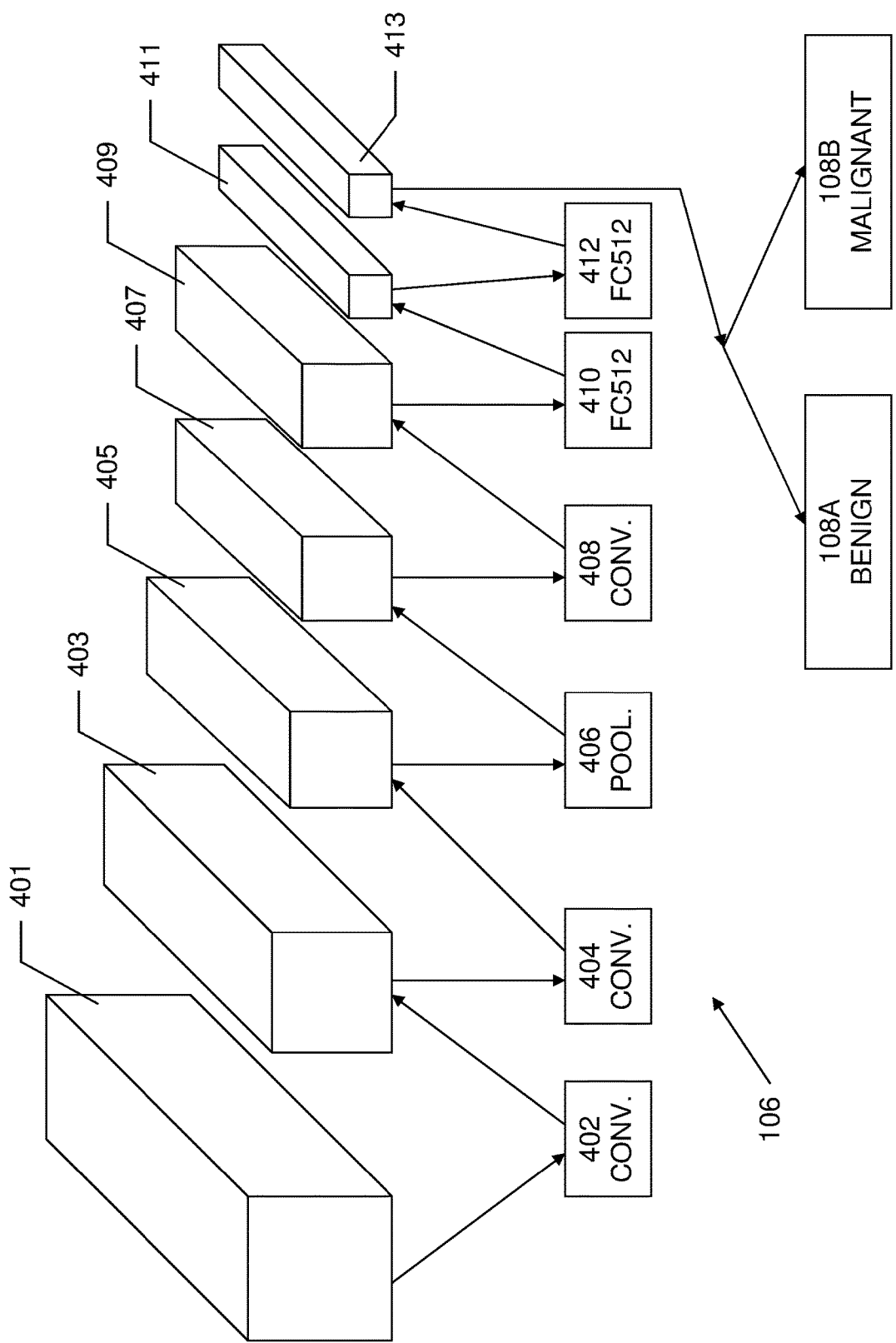
FIG. 4 illustrates an exemplary diagram of layers of processing in a classification network.

Returning to FIG. 2, at 214, the output of 212 may be input to a classification network 106, in order to classify the entire image as containing or not containing a feature of interest, such as certain types of lesions, for example, a malignant tumor. Turning to FIG. 4, classification network 106 may include processing layers such as convolutions, REctifying Linear Units (RELUs), fully connected layers, and max-pooling operations, in order to decrease the spatial dimensions to a single pixel. For example, a first convolutional layer 402 may receive a set of feature vectors 401, may employ 256 filters, and may generate a set of feature vectors 403. A second convolutional layer 404 may receive the set of feature vectors 403, may employ 128 filters, and may generate a set of feature vectors 405. A max-pooling layer 406 may receive a set of feature vectors 405 and may generate a set of feature vectors 407. A third convolutional layer 408 may receive the set of feature vectors 407, may employ 256 filters, and may generate a set of feature vectors 409. Two fully connected (FC) layers 410, 412 may employ 512 filters each and may perform the final classification yielding a singular output 412, corresponding to the probability of presence of absence of a benign tumor 108A or a malignant tumor 108B.

As an example of use of the described techniques, the techniques may be applied to a mammogram data set of 796 patients with 80 positive (164 images), with confirmed carcinoma (BIRADS 5) and 716 negative (1869 images) belonging to normal patients as well as benign findings with BIRADS 1, 2. As a baseline, the techniques may be tested with a naive approach using a pre-trained network. This approach, known as transfer learning, may be used to train a CNN on a publicly available rich source of data, such as the ImageNet. ImageNet is a publicly available database of images, which contains a labeled data set of a large number of natural images in many different classes. The last fully-connected layers, which output the class scores, may be removed, treating the rest of the CNN as a fixed feature extractor for a new dataset. A pre-trained VGG16 network may be used for image representation, resulting in a feature vector of 4096D for each input mammogram. The VGG16 network may contain 16 learned layers composed of 13 convolutional layers and 3 fully-connected layers. In order to fit the mammogram images into the network, the image tiles may be downsized and the color mode and bits-per-pixel may be transformed. Five-fold cross validation may be used to evaluate model performance.

Data for binary classification often exhibits a highly skewed class distribution, for example, most samples may belong to a majority class while in the minority class there may be only a scarce amount of samples. In computer vision, this problem appears in various detection problems such as object and semantic edge detection. In the medical domain this class imbalance arises naturally as the number of healthy (normal) cases are commonly orders of magnitude higher than ill (positive) patients with a certain disease. The area under the Receiver Operator Characteristics (ROC) curve, namely AUC, on the other hand, is insensitive to class population because the ROC curve specifies the relationship between false-positive rate (FPR) and true-positive rate (TPR), which are normalized measures. In embodiments, the AUC optimization may be directly enforced in deep CNN models to cope with highly imbalanced data sets.

Convolutional neural networks may be expressed as the composition of functions, each representing a layer in the network, and the output to a given input x may be written in terms of the function $f$ as $$f(x) = (f_L(w_L) \circ f_{L-1}(w_{L-1}) \circ \ldots \circ f_1(w_1))(x), \quad (1)$$

where $w_l$ denotes the weights of the $l^{th}$ layer, and each layer computes the input of the following one, such as $x_{l+1} = f_l(x_l)$. The $(L-1)^{th}$ layer typically computes the score of the input x, $x_L = f_{L-1}(x)^2$, and it is fed into the last layer to obtain the loss, $f_L(x_L)$. Typically, this loss is just the $\ell_2$ difference between the label and the obtained probability. However, in embodiments, a cost function that maximizes the AUC may be used.

Consider the scenario of a set of $N^+$ training examples $x_i$ from a positive (minority) class, and $N^-$ examples $x_j$ from a negative (majority) class, for example, where $N^- > N^+$. The training set is thus given by the set $\{(x_i, y_i)\}_{i=1 \ldots N}$, where $y_i \in \{1, -1\}$. Considering the general classifier function $f$, the AUC may be estimated through the Mann-Whitney statistic, given by $$AUC = \frac{1}{N^+ N^-} \sum_{i=1}^{N^+} \sum_{j=1}^{N^-} \mathbb{1}(f(x_i) > f(x_j)), \quad (2)$$

where $\mathbb{1}$ is the indicator function. The loss function may be defined by means of appropriate function g, which penalizes cases where $f(x_i) < f(x_j)$ and adding an $\ell 2$ regularization term on the network weights, symbolically represented by W, such as $$\mathcal{L}(W) = \frac{\lambda}{2} \|w\|_2^2 + \frac{1}{N^+ N^-} \sum_{i=1}^{N^+} \sum_{j=1}^{N^-} g(x^i, x^j). \quad (3)$$

Moving to an online optimization scheme, the above loss can be modified to the sum of a loss over individual samples during training at time t, such as $\mathcal{L}(W) = \sum_{t=1}^{T} \mathcal{L}_t(W)$. Therefore, for every sample $(x^t, y^t)$, the loss computed by the last layer of the CNN may be defined as $$f_L(x_L^t, y^t) = \quad (4)$$

$$\frac{1}{2} \|w\|_2^2 + I_{(y^t=1)} \frac{1}{N^-} \sum_{j=1}^{N^-} \ell(x_L^t, x_L^j) + I_{(y^t=-1)} \frac{1}{N^+} \sum_{i=1}^{N^+} \ell(x_L^i, x_L^t).$$

When the above function $\ell$ is a step function of the difference $(x_L^j - x_L^t)$, the expression in Equation (4) effectively maximizes an online estimation of the AUC. Intuitively, the function $\ell(x^i, x^j)$ penalizes cases where a positive sample $x^i$ receives a lower score than a negatives sample $x^t$. This function may be defined by a variant of the logistic function, $$\ell(x^i, x^j) = -\log\left(\frac{1}{1 + e^{(x^j - x^i)}}\right).$$

To employ back propagation, one only needs to compute $\delta f_L/\delta x_L$, which reduces to the sum of the terms $$\frac{\partial \ell}{\partial x_L}.$$

These partial derivatives are typically simple to compute, as they are simply the derivatives of a shifted logistic function.

Note that this loss should be computed in a pair-wise manner: each sample x depends also on other samples $x^i$ from the opposite class, and keeping these in memory is often infeasible. This is not a problem in the deep learning framework, as only the gradient of $f_L$ with respect to $x_L^i$ is needed, and not with respect to the high dimensional vectors $x^i$. Since these elements $x_L^i$ are scalars (simply the values assigned to each previously seen sample), they can be easily stored in memory. According, embodiments may keep, for example, two buffers of positive and negative classes, $S^+=\{(x_L^i:y^i=1\}$ and $S^-=\{x_L^i:y^i=-1\}$ with which one can compute Equation (4).

Figure 5:
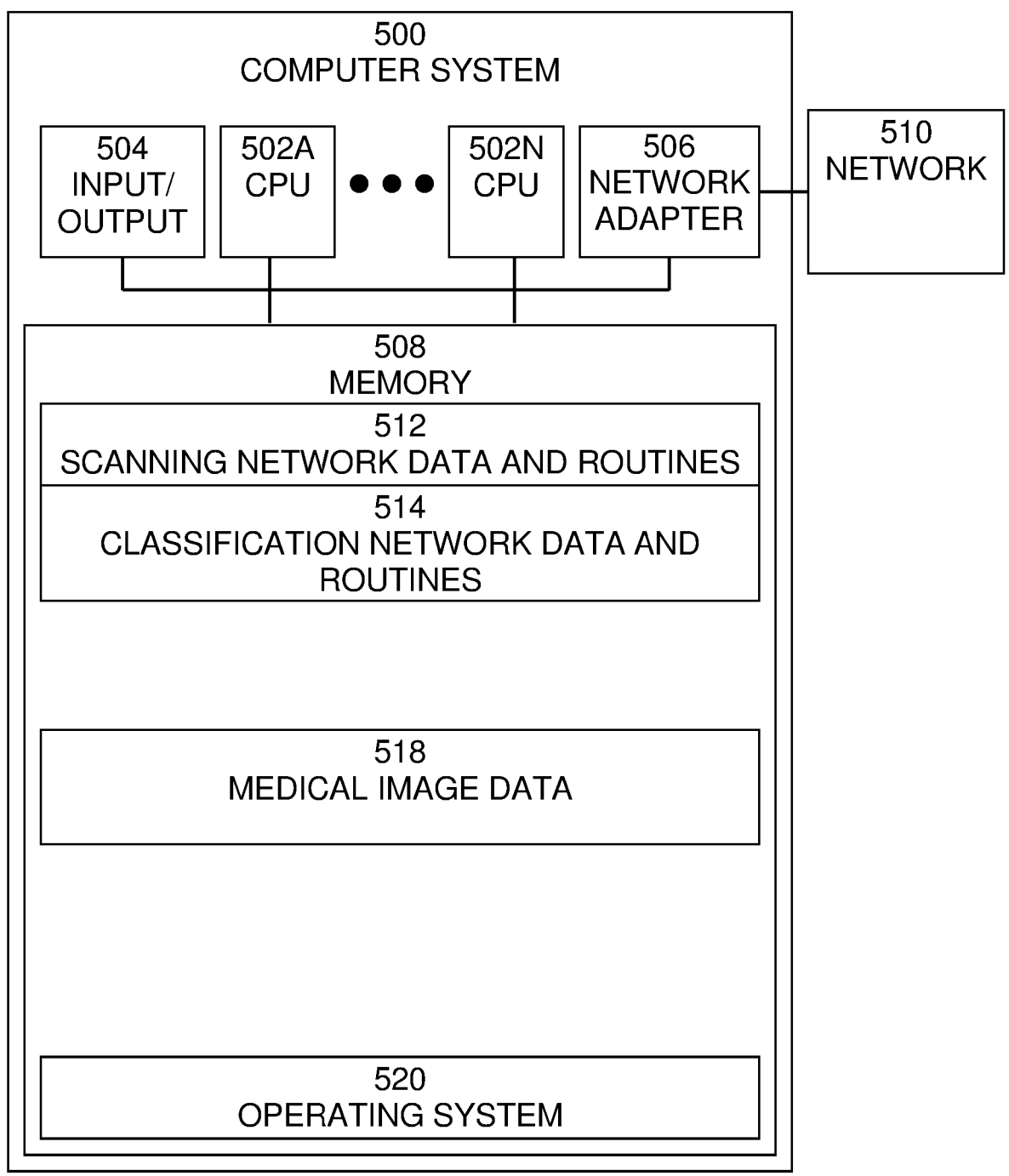
FIG. 5 is an exemplary block diagram of a computer system in which processes involved in the embodiments described herein may be implemented.

An exemplary block diagram of a computer system 500, in which processes involved in the embodiments described herein may be implemented, is shown in FIG. 5. Computer system 500 may typically be implemented using one or more programmed general-purpose computer systems, such as embedded processors, systems on a chip, personal computers, workstations, server systems, and minicomputers or mainframe computers, or in distributed, networked computing environments. Computer system 500 may include one or more processors (CPUs) 502A-502N, input/output circuitry 504, network adapter 506, and memory 508. CPUs 502A-502N execute program instructions in order to carry out the functions of the present communications systems and methods. Typically, CPUs 502A-502N are one or more microprocessors, such as an INTEL CORE® processor. FIG. 5 illustrates an embodiment in which computer system 500 is implemented as a single multi-processor computer system, in which multiple processors 502A-502N share system resources, such as memory 508, input/output circuitry 504, and network adapter 506. However, the present communications systems and methods also include embodiments in which computer system 500 is implemented as a plurality of networked computer systems, which may be single-processor computer systems, multi-processor computer systems, or a mix thereof.

Input/output circuitry 504 provides the capability to input data to, or output data from, computer system 500. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 506 interfaces device 500 with a network 510. Network 510 may be any public or proprietary LAN or WAN, including, but not limited to the Internet.

Memory 508 stores program instructions that are executed by, and data that are used and processed by, CPU 502 to perform the functions of computer system 500. Memory 508 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 508 may vary depending upon the function that computer system 500 is programmed to perform. In the example shown in FIG. 5, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present communications systems and methods may include any and all such arrangements.

In the example shown in FIG. 5, memory 508 may include scanning network data and routines 512, classification network data and routines 518, medical image data 518, and operating system 512. Scanning network data and routines 512 may include data and software routines to perform processing to implement a plurality of convolutional layers and may generate data to be stored. Classification network data and routines 518 may include data and software routines to perform processing to implement processing layers such as convolutions, max-pooling operations, REctifying Linear Units (RELUs) and fully connected networks, and may generate data to be stored. Medical image data 518 may include data relating to a plurality of medical images, such as digital images received from a medical imaging system or a medical database system for classification. Medical image data 518 may be in any standard, non-standard, proprietary, or non-proprietary image format or file format. Operating system 520 may provide overall system functionality.

As shown in FIG. 5, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multi-tasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A computer-implemented method for classifying medical images comprising:
   receiving a plurality of image tiles from a whole medical image, the whole medical image having a global image-level tag and without local annotations that reveal a position and a shape of findings within the image, each image tile including a portion of the whole image, processed by a trained or a pre-trained model and outputting a one-dimensional feature vector for each tile to generate a three-dimensional feature volume; and
   classifying the whole image by a trained model based on the generated three-dimensional feature volume to form a classification of the image, the trained model comprising a plurality of layers to decrease spatial dimensions of the generated three-dimensional feature volume to a singular output.

2. The method of claim 1, wherein the whole image is one of a mammogram image or a breast Magnetic Resonance Imaging image.

3. The method of claim 2, wherein the singular output is a classification that is a binary classification that classifies the images into malignant or benign.

4. The method of claim 3, wherein the class populations are highly imbalanced.

5. The method of claim 3, wherein the three-dimensional feature volume is generated using a plurality of layers of convolutional network processing in a deep convolutional neural network, wherein the deep convolutional neural network uses a deep neural network loss function that directly maximizes an area under the curve (AUC) performance measure.

6. The method of claim 5, wherein the deep convolutional neural network combines a tile based approach with pre-trained encoding and trained convolutional neural network layers.

7. The method of claim 1, wherein sizes of the tiles are determined based on an expected size of findings in the images.

8. A system for classifying medical images, the system comprising a processor, memory accessible by the processor, and computer program instructions stored in the memory and executable by the processor to perform:
   receiving a plurality of image tiles from a whole medical image, the whole medical image having a global image-level tag and without local annotations that reveal a position and a shape of findings within the image, each image tile including a portion of the whole image, processed by a trained or a pre-trained model and outputting a one-dimensional feature vector for each tile to generate a three-dimensional feature volume; and
   classifying the whole image by a trained model based on the generated three-dimensional feature volume to form a classification of the image, the trained model comprising a plurality of layers to decrease spatial dimensions of the generated three-dimensional feature volume to a singular output.

9. The system of claim 8, wherein the whole image is one of a mammogram image or a breast Magnetic Resonance Imaging image.

10. The system of claim 9, wherein the singular output is a classification that is a binary classification that classifies the images into malignant or benign.

11. The system of claim 10, wherein the class populations are highly imbalanced.

12. The system of claim 10, wherein the three-dimensional feature volume is generated using a plurality of layers of convolutional network processing in a deep convolutional neural network, wherein the deep convolutional neural network uses a deep neural network loss function that directly maximizes an area under the curve (AUC) performance measure.

13. The system of claim 12, wherein the deep convolutional neural network combines a tile based approach with pre-trained encoding and trained convolutional neural network layers.

14. The system of claim 8, wherein sizes of the tiles are determined based on an expected size of findings in the images.

15. A computer program product for classifying medical images, the computer program product comprising a non-transitory computer readable storage having program instructions embodied therewith, the program instructions executable by a computer, to cause the computer to perform a method comprising:
   receiving a plurality of image tiles from a whole medical image, the whole medical image having a global image-level tag and without local annotations that reveal a position and a shape of findings within the image, each image tile including a portion of the whole image, processed by a trained or a pre-trained model and outputting a one-dimensional feature vector for each tile to generate a three-dimensional feature volume; and
   classifying the whole image by a trained model based on the generated three-dimensional feature volume to form a classification of the image, the trained model comprising a plurality of layers to decrease spatial dimensions of the generated three-dimensional feature volume to a singular output.

16. The computer program product of claim 15, wherein the whole image is one of a mammogram image or a breast Magnetic Resonance Imaging image.

17. The computer program product of claim 16, wherein the singular output is a classification that is a binary classification that classifies the images into malignant or benign.

18. The computer program product of claim 17, wherein the class populations are highly imbalanced.

19. The computer program product of claim 17, wherein the three-dimensional feature volume is generated using a plurality of layers of convolutional network processing in a deep convolutional neural network, wherein the deep convolutional neural network uses a deep neural network loss function that directly maximizes an area under the curve (AUC) performance measure.

20. The computer program product of claim 19, wherein the deep convolutional neural network combines a tile based approach with pre-trained encoding and trained convolutional neural network layers.

* * * * *